(12) United States Patent
Muderlak

(10) Patent No.: US 11,796,219 B2
(45) Date of Patent: Oct. 24, 2023

(54) COMBINED AIR AND AIR TREATMENT PREPARATION DISPENSER

(71) Applicant: Xela Innovations, LLC, Glendale, WI (US)

(72) Inventor: Todd J. Muderlak, Whitefish Bay, WI (US)

(73) Assignee: Xela Innovations, LLC, Glendale, WI (US)

( * ) Notice: Subject to any disclaimer, the term of this patent is extended or adjusted under 35 U.S.C. 154(b) by 814 days.

(21) Appl. No.: 16/664,142

(22) Filed: Oct. 25, 2019

(65) Prior Publication Data
US 2020/0132336 A1 Apr. 30, 2020

Related U.S. Application Data

(60) Provisional application No. 62/751,944, filed on Oct. 29, 2018.

(51) Int. Cl.
| | |
|---|---|
| *F24F 13/08* | (2006.01) |
| *A47K 10/48* | (2006.01) |
| *F24F 13/20* | (2006.01) |
| *F16K 31/06* | (2006.01) |
| *F24F 8/108* | (2021.01) |

(52) U.S. Cl.
CPC ............ *F24F 13/085* (2013.01); *A47K 10/48* (2013.01); *F16K 31/0644* (2013.01); *F24F 8/108* (2021.01); *F24F 2013/205* (2013.01)

(58) Field of Classification Search
CPC .......... F24F 13/08; F24F 13/085; F24F 8/108; F24F 2013/205; F16K 31/0644; A47K 10/48

USPC ....................................................... 55/385.2
See application file for complete search history.

(56) References Cited

U.S. PATENT DOCUMENTS

| | | | | |
|---|---|---|---|---|
| 4,383,377 | A * | 5/1983 | Crafton | A47K 10/48 34/90 |
| 2005/0076529 | A1* | 4/2005 | Holmes | A47K 10/48 34/90 |
| 2011/0114669 | A1* | 5/2011 | Yang | A47K 5/16 222/639 |

FOREIGN PATENT DOCUMENTS

GB 2413283 10/2005

OTHER PUBLICATIONS

PCT/US2019/058156 International Search Report and Written Opinion of file Searching Authority dated Jan. 8, 2020 (14 pages).

\* cited by examiner

*Primary Examiner* — Avinash A Savani
*Assistant Examiner* — Dana K Tighe
(74) *Attorney, Agent, or Firm* — Amundsen Davis, LLC

(57) ABSTRACT

An apparatus for dispensing air and an air treatment preparation includes a drying module, an air treatment preparation module, and an air diverter. The drying module has an air dispensing outlet and an air diverter outlet. The air treatment preparation module has an air diverter inlet and an air treatment preparation. The air diverter has a one-way valve. The air diverter connects the air diverter outlet of the drying module to the air diverter inlet of the air treatment preparation module via the one-way valve.

10 Claims, 19 Drawing Sheets

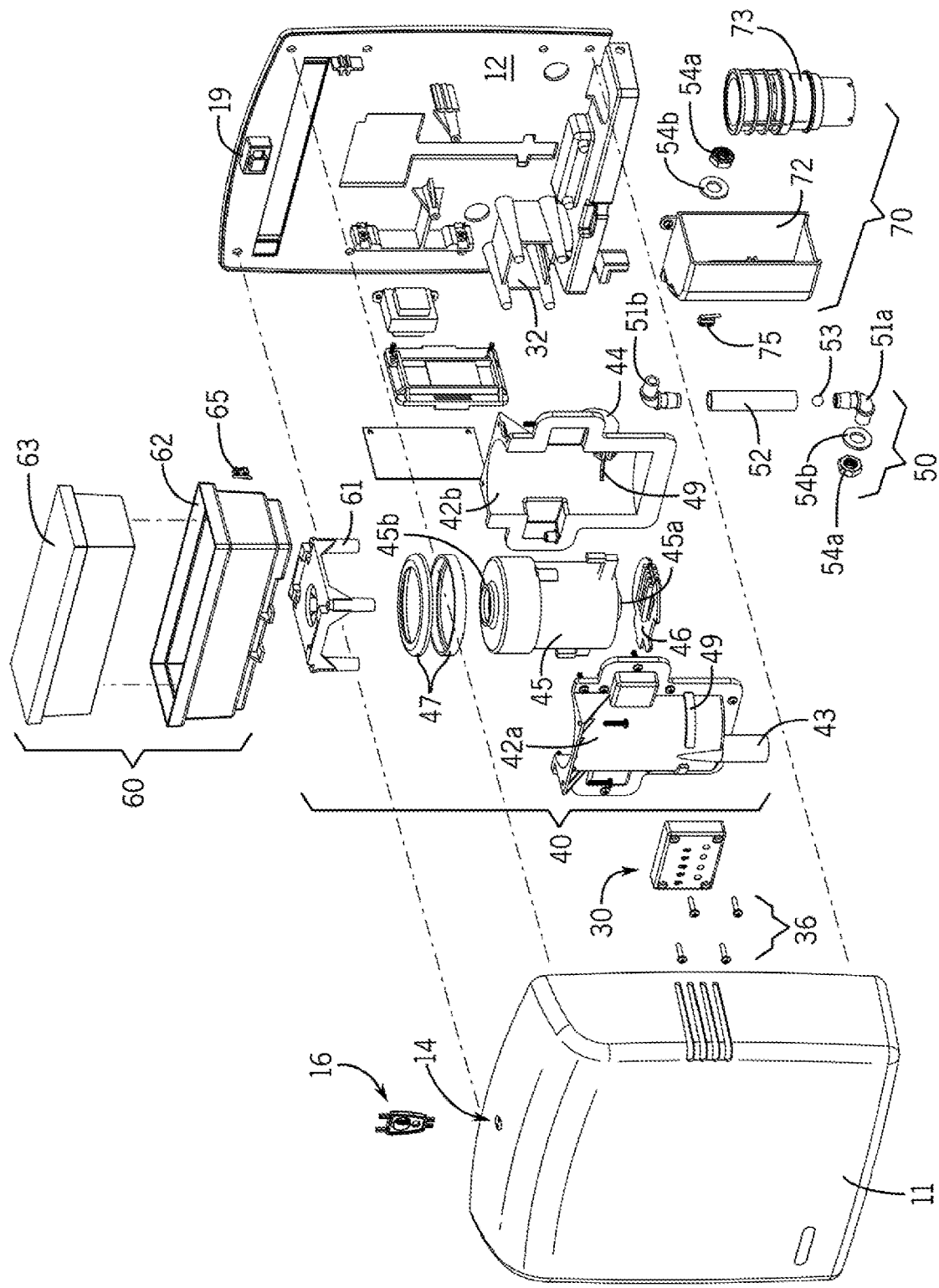

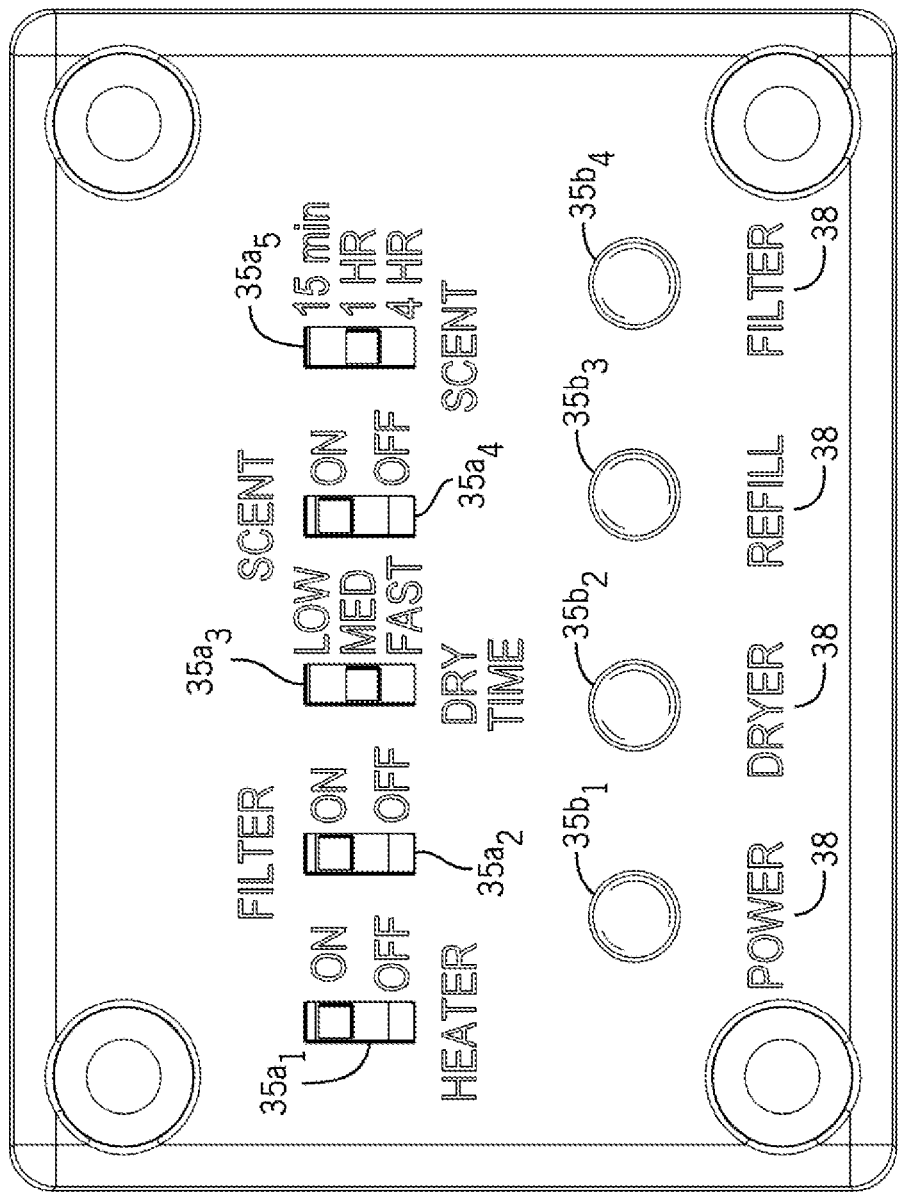

COMBINED AIR AND AIR TREATMENT PREPARATION DISPENSER

FIELD

Embodiments of this disclosure relate to hand dryers, and more particularly to hand dryers which also provide an air treatment preparation, such as an air fragrance or air deodorizer.

BACKGROUND

Hand dryers are found in many washrooms and other locations. These hand dryers pull air from the immediate area, in some instances filter and/or heat the air, and force the air through a nozzle outlet to provide drying, e.g., for a user's hands. Some hand dryers incorporate an air treatment preparation, such as an air fragrance or air deodorizer. However, such devices have a single outlet for both the drying air and the air treatment. As a result, individuals drying their hands are also in contact with the air treatment preparation (e.g., air fragrance or air deodorizer). This can cause problems for individuals with sensitive skin, wounds or breathing difficulties.

Further, space in washrooms, and particularly commercial washrooms, is limited. Hand driers must be easy to access and yet not hinder ingress or egress of visitors. Hand driers should be compact. Some existing hand driers which incorporate an air treatment preparation expel the air treatment through an outlet separate from that which dispenses air for drying hands use a secondary motor to power the expulsion the air treatment preparation, adding weight, size and cost to the hand drier. Further, with an additional motor, there are more moving parts which require maintenance.

It would be desirable to provide a hand drying apparatus which includes air treatment preparation which solves one or more of the above deficiencies.

SUMMARY

Embodiments of the present disclosure provide an apparatus for dispensing air and an air treatment preparation. According to embodiments of the present disclosure, an apparatus for dispensing air and an air treatment preparation comprises a drying module comprising an air dispensing outlet and an air diverter outlet; an air treatment preparation module comprising an air diverter inlet and an air treatment preparation; and an air diverter comprising a one-way valve, wherein the air diverter connects the air diverter outlet of the drying module and the air diverter inlet of the air treatment preparation module via the one-way valve.

In further embodiments, the present disclosure provides an apparatus for dispensing air and an air treatment preparation comprising a housing having a housing back panel and a housing cover releasably attached to the housing back panel, wherein the housing cover includes a bottom panel having an opening and a side panel having a plurality of vents; a drying module having an inlet, an air dispensing outlet, and an air diverting outlet, wherein the air dispensing outlet is aligned with the opening in the bottom panel of the housing cover; an air treatment preparation module having an air diverting inlet and an air treatment preparation, wherein the air treatment preparation is exposed to the plurality of vents; and an air diverter connecting the air diverting outlet and air diverting inlet, the air diverter further including a one-way valve.

In further embodiments, the present disclosure provides a method of dispensing an air treatment preparation. In accordance with embodiments of the present disclosure, the method comprises activating an apparatus comprising a drying module comprising a motor, an air dispensing outlet and an air diverter outlet, an air treatment preparation module comprising an air diverter inlet and an air treatment preparation, and an air diverter connecting the air diverter outlet of the drying module and the air diverting inlet of the air treatment preparation module; forcing air, using the motor, through the drying module, wherein a majority portion of the air is forced through the air dispensing outlet and a minor portion of the air is forced through the air diverter inlet; building air pressure in the air diverter to reach a threshold level to open the one-way valve; opening the one way valve, thereby permitting air flow through the air diverter and into the air treatment preparation module; contacting the air treatment preparation with at least a portion of the minor portion of the air; and forcing the minor portion of the air out of the air treatment preparation module.

BRIEF DESCRIPTION OF THE DRAWINGS

Preferred embodiments of the disclosure are described below with reference to the following accompanying drawings, which are for illustrative purposes only. Throughout the following views, the reference numerals will be used in the drawings, and the same reference numerals will be used throughout the several views and in the description to indicate the same or like parts.

FIG. 4 is an exploded view of the apparatus, in accordance with embodiments of the present disclosure;

FIG. 6 shows the indicator and control panel cover in further detail, in accordance with embodiments of the present disclosure, in accordance with embodiments of the present disclosure;

DETAILED DESCRIPTION

Figure 1A:
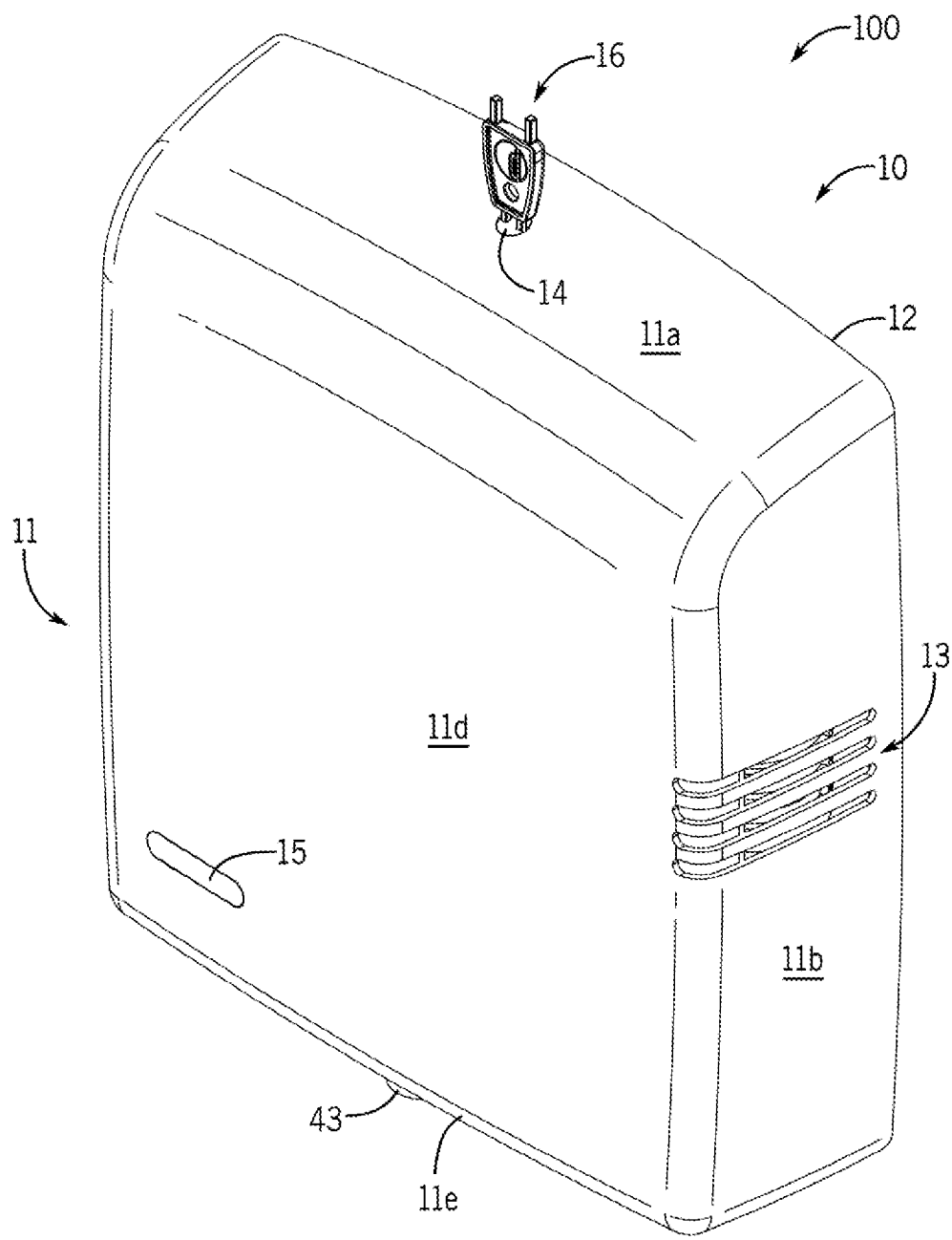
FIG. 1A is a perspective view of an embodiment of an apparatus for dispensing air and an air treatment preparation in accordance with embodiments of the present disclosure.
Figure 1B:
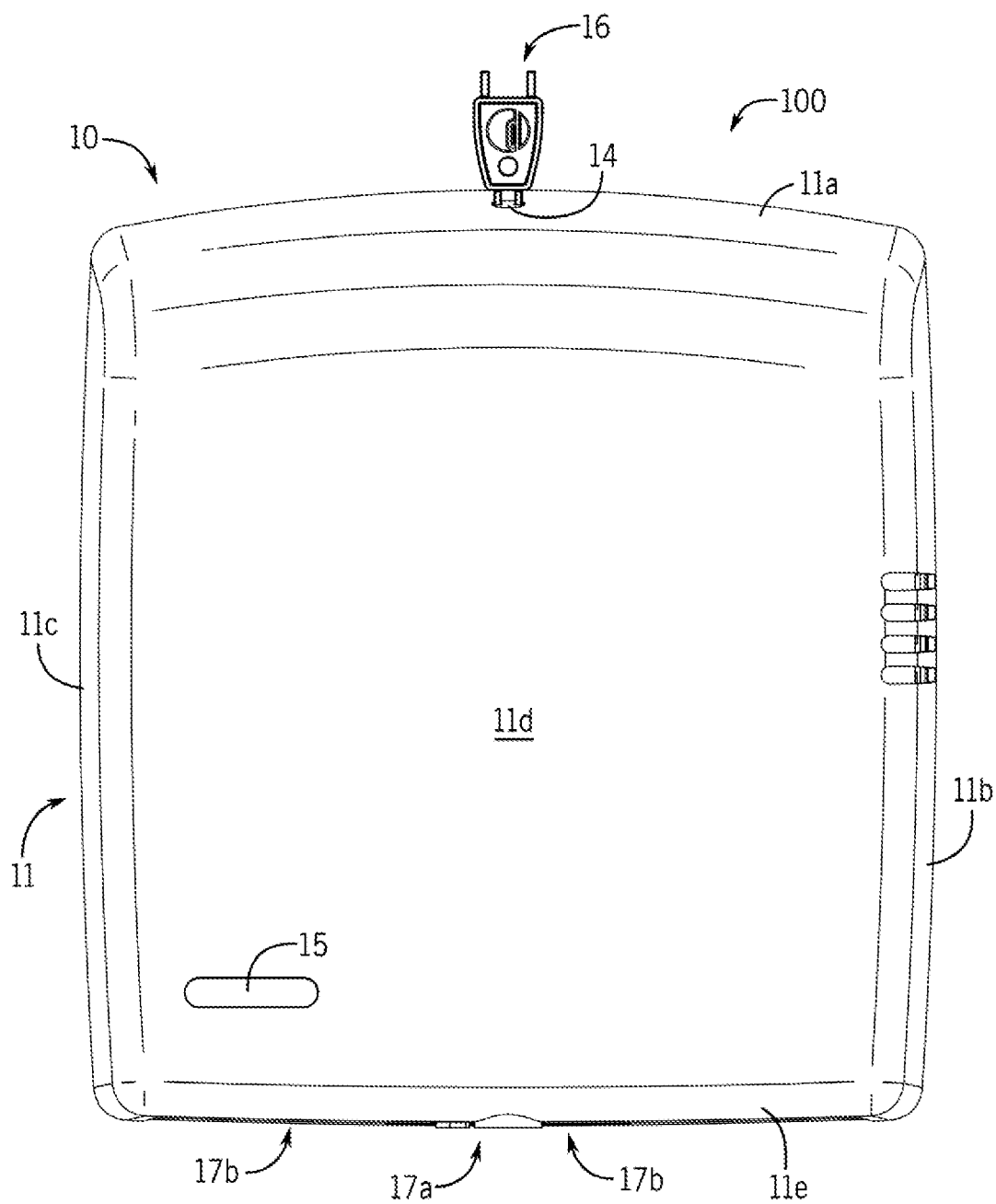
FIG. 1B is a front view of the embodiment shown in FIG. 1A, in accordance with embodiments of the present disclosure.

Embodiments of the disclosure relate to an apparatus for dispensing air and an air treatment preparation. The apparatus can be mounted on a wall, cabinet, or other substrate that provides the ability to dispense air and an air treatment preparation to a user.

FIGS. 1A-1F show various view of the housing 10 for an apparatus for dispensing air and an air treatment preparation 100 in accordance with embodiments of the present disclosure. The apparatus 100 includes a housing 10 which is made up of the housing cover 11 and the housing back panel 12. The housing cover 11 has an upper panel 11a, a right side panel 11b, a left side panel 11c, a front panel 11d and a bottom panel 11e. The upper panel 11a includes a key port 14 which is configured to receive a key 16 to open the housing 10. However, in other embodiments, the housing 10 may be configured to open through other mechanisms, including keyless mechanisms such as push features. The right side panel 11b includes a plurality of vents 13 through which the air treatment preparation is dispersed. While in the embodiment shown the plurality of vents 13 is illustrated as a plurality of horizontally disposed slit-like vents, the vents may take other forms, shapes and configurations provided the vents 13 align with the air treatment preparation module 70, as will be further shown and described herein.

The front panel 11d includes a viewing port 15, generally an opening in the front panel 11d which is covered with a transparent or translucent material which protects the inside of the apparatus 100 from debris and moisture and through which one or more indicators 35b may be viewed. It will be appreciated that the location, shape and size of the viewing port 15 may vary by convenience and design depending on the specific location, shape and size of the control panel 34, as further shown and described herein.

The bottom panel 11e includes an opening 17a through which the air dispensing outlet 43 is disposed. The air dispensing outlet 43 dispenses untreated air (air which has not been in contact with an air treatment preparation) is dispensed, e.g., to dry a user's hands. On either side of the opening 17a is an air inlet 17b through which air is brought into the apparatus 100.

The housing cover 11 as shown in FIGS. 1A-1F is in the closed position. In other words, the housing cover 11 is secured to the housing back panel 12 with the interior components housed within. In FIGS. 2A-2C, the housing cover 11 is shown in the open position. That is, the housing cover 11 has been opened (unlocked, if necessary) and pivoted downward away from the housing back panel 12 at pivots 18. It will be appreciated that, while only a single pivot 18 is visible in the embodiments shown in FIGS. 2A-2C, a second pivot is provided between the housing cover 11 and housing back panel 12 opposite so as to be symmetrical with the visible pivot 18.

Also visible in FIGS. 2A-2C is the lock 19 which interfaces with the key port 14 on the housing cover 11 to secure the housing cover 11 to the housing back panel 12. In the embodiment shown, the key lock release (or other form of keyless release) used with the apparatus 100, along with the pivoting of the housing described in further detail below, allows for quicker and easier access to the internal features of the apparatus. This saves time, and therefore money, when attending to replacement of components (e.g., filter(s), air treatment preparations, etc.) and/or repair.

The housing 10 protects the apparatus' 100 interior components, including the control module 30, drying module 40, filter module 60 with switch 65 and air treatment preparation module 70 with switch 75.

Figure 3:
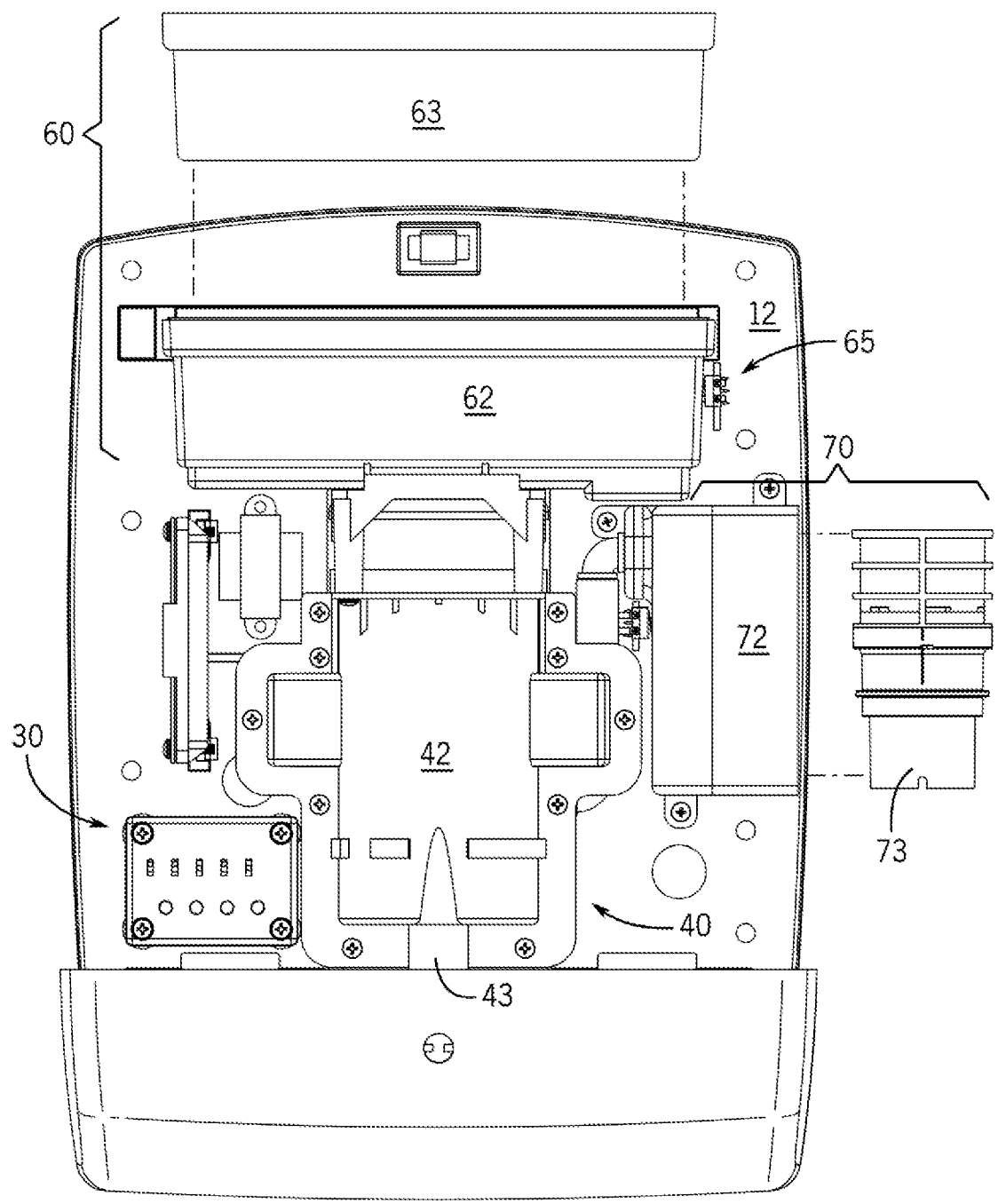
FIG. 3 is a front view of the embodiment shown in FIG. 2A with the filter and air treatment preparation assembly removed, in accordance with embodiments of the present disclosure.

As shown more fully in FIGS. 3-4, the filter module 60 includes a filter module housing 62 which houses a filter 63, such as a fibrous filter or a HEPA filter and connects to the inlet (not shown) of the drying module 40 to filter air as it is pulled into the apparatus 100. The air treatment preparation module 70 includes an air treatment preparation housing 72 which houses an air treatment preparation assembly 73. As used herein, an "air treatment preparation" refers to a substance which freshens, scents, deodorizes, and/or sanitizes air upon being dispensed into the air, such as to control odors. Nonlimiting examples of air treatment preparations include air fresheners, air deodorizers, air sanitizers, odor masking preparations and combinations thereof. Air treatment preparations can take any form, e.g., oils, aerosols, beads, gels, sprays, wax, provided at least a portion of the air treatment preparation is dispensed into the air when contacted with airflow. An air treatment preparation does not include filters or other structures which remove particulate from air. As used herein, an "air treatment preparation assembly" is the structure or combination of structures which contains, confines, meters, portions or otherwise holds the air treatment preparation. For example, when the air treatment preparation is in liquid form, the air treatment preparation assembly is the bottle or container which holds the liquid, including any wick or wick-like component, and which is secured into the air treatment preparation module 70. Air treatment preparation assemblies therefore include, by way of nonlimiting examples, air treatment preparation housings, containers, wicks, straws, hoses, cans, pumps and pump-like structures, cartridges, and other similar structures which contain air treatment preparations and/or move or assist in moving a quantity of air treatment preparation to a location to be contacted by air for dispersal.

The specific components of the apparatus 100 will now be discussed in further detail.

The control module 30 includes a control module housing 32, a control module covering 33 and a control panel 34, as shown in further detail in FIGS. 4-6. The control module covering 33 and control panel 34 are secured to one another and the housing 32 using at least one connection member 36, such as a bracket, interconnecting features, nail, clip, or, such as in the embodiment shown, screw. Specifically, in the embodiment shown, the control module housing 32, control module covering 33 and control panel 34 are secured to one another using a plurality of screws 36.

In the embodiment shown, the control module housing 32 is provided as a structure integral with the housing back panel 12. As will be appreciated, there are certain manufacturing benefits to having the control module housing 32 as an integral formation with the housing back panel 12, including, for example, less separate parts required for assembly. However, in further embodiments, the control module housing 32 may be provided as a separate and distinct component and secured within the housing 10 using known structures and devices.

Figure 5A:
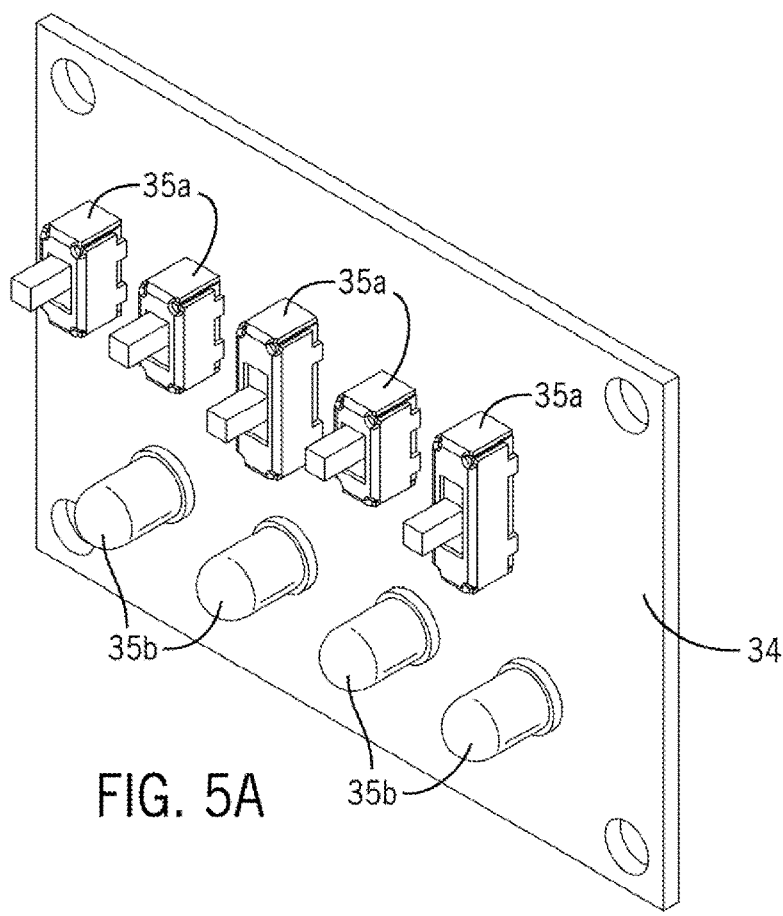
FIG. 5A is a perspective view of the indicator and control panel, in accordance with embodiments of the present disclosure, in accordance with embodiments of the present disclosure.
Figure 5B:
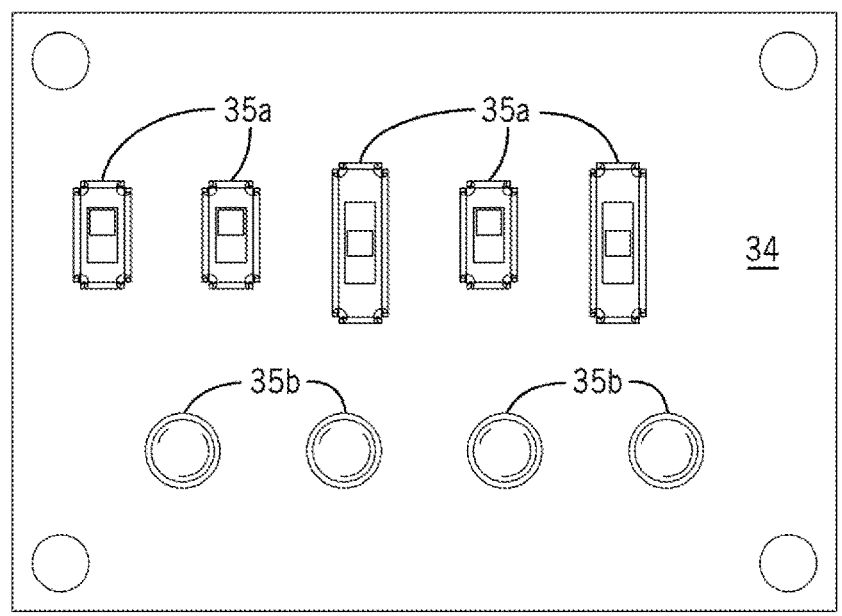
FIG. 5B is a front view of the indicator and control panel, in accordance with embodiments of the present disclosure.

With particular reference to FIGS. 5A-5B, the control panel 34 includes a plurality of controls 35a and indicators 35b. In the embodiment shown, the controls 35a are each switches having at least two operable positions. Some controls 35a may have three or more operable positions or, in some embodiments, be infinitely adjustable over a defined range. In still further embodiments, one or more of the controls 35a may be a knob, button, slide, or any other structure or device having at least two operable positions. As used herein, the term "operable position" refers to a stationary location of a control which sets a path for or disrupts a path of electric current.

The controls 35a each control a function of the apparatus 100 and allow a user to customize the operation of the apparatus 100. For example, and as will be described in further detail with reference to FIG. 6, in some embodiments, a control 35a may be provided to control at least one function of heating, fan speed, duration of fan activation, air diversion, timing of automatic activation, and reminders for changing filters/air treatment preparations.

In the embodiment shown, the indicators 35b are LEDs; however, in further embodiments, the indictors 35b may take any form which presents a visual cue (e.g., LCD screen, three-dimensional indicator like a push button). In some embodiments, one or more of the indicators 35b may be configured to change status (e.g., light up or turn off) in response to a particular operable position of a corresponding control 35a. In alternative embodiments, the indicators 35b may be configured to change status (e.g., light up or turn off) in response to conditions of the apparatus 100 and not in response to a particular operable position of any of the controls 35a. In some embodiments, one or more indicators 35b may be further configured with an audible indicator such as a beep, chirp or other noise.

Turning to FIG. 6, the control module covering 33 provides the labels 38 for the controls 35a and indicators 35b. Labels 38 identify the function of the controls 35a and the condition communicated by the indicators 35b. As shown in FIG. 6, the labels 38 are text. However, in further embodiments, the labels 38 can be graphic representations of the corresponding functions/conditions or a combination of text and graphic representations.

In the particular embodiment shown, control $35a_1$ turns the heater of the motor on and off. In other words, control $35a_1$ has two operable positions, one (as presently shown) in which the heater is functional and a second in which the heater is not functional. There is no indicator corresponding to the function of control $35a_1$.

Control $35a_2$ turns the filter module switch 65 on and off. Referring to FIGS. 2A-2B, the filter module 60 includes switch 65. Switch 65 indicates the presence or absence of a filter in the filter module 60 and/or functions as a timer to prompt the changing or replacing of a filter in the filter module 60. For example, when a filter is placed in the filter module 60, the switch 65 registers the presence of the filter (and, in some embodiments, signals the presence of the filter, e.g., by way of an indicator 35b, as discussed in further detail below) and, when a timing functionality is included in the switch 65, resets to a starting time. When the final time is reached (e.g., 30 days, 60 days, etc.), the switch 65 signals (e.g., by way of an indicator 35b, discussed in further detail below) that it is time to change the filter. When the used filter is removed from the filter module 60, in some embodiments, the switch 65 may signal the absence of the filter (e.g., by way of an indicator 35b, as discussed in further detail below). The placement of a new filter restarts the cycle.

With control $35a_2$ in the "on" position, such as shown in FIG. 6, the switch 65 is active to communicate the condition of the filter as programmed, e.g., present or absent, time to replace, etc. When the control $35a_2$ is in the "off" position, the switch 65 is inactive and does not communicate the condition of the filter as programmed, e.g., present or absent, time to replace, etc.

In the particular embodiment shown herein, the switch 65 is in communication with indicator $35b_4$. That is, when the switch 65 activates to signal the status of the filter as programmed, e.g., present or absent, time to replace, etc., the indicator $35b_4$ changes status, e.g., lights up or turns off.

Control $35a_3$ changes the fan speed and, thereby, the time needed to dry a user's hands, as indicated by the label "DRY TIME." As will be appreciated, a low fan speed will require a longer dry time, while a fast fan speed requires a shorter dry time. In the embodiment shown, the control $35a_3$ is in the "MED" or medium position and two other operable positions, corresponding to "LOW" and "FAST" are available. In further embodiments, the control $35a_3$ may have more than three operable positions to provide additional adjustment of the fan speed.

Much like control $35a_2$, control $35a_4$ is in communication with air treatment preparation switch 75. Control $35a_4$ turns the air treatment preparation module switch 75 on and off. Referring to FIGS. 2A-2B, the air treatment preparation module 70 includes switch 75. Switch 75 indicates the presence or absence of an air treatment preparation in the air treatment preparation module 70 and/or functions as a timer to prompt the changing or replacing of an air treatment preparation in the filter module 70. For example, when an air treatment preparation is placed in the air treatment preparation module 70, the switch 75 registers the presence of the air treatment preparation (and, in some embodiments, signals the presence of the air treatment preparation, e.g., by way of an indicator 35b, as discussed in further detail below) and, when a timing functionality is included in the switch 75, resets to a starting time. When the final time is reached (e.g., 30 days, 60 days, etc.), the switch 75 signals (e.g., by way of an indicator 35b, discussed in further detail below) that it is time to change the air treatment preparation. When the used air treatment preparation is removed from the air treatment preparation module 70, in some embodiments, the switch 75 may signal the absence of the air treatment preparation (e.g., by way of an indicator 35b, as discussed in further detail below). The placement of a new air treatment preparation restarts the cycle.

With control $35a_4$ in the "on" position, such as shown in FIG. 6, the switch 75 is active to communicate the condition of the air treatment preparation as programmed, e.g., present or absent, time to replace, etc. When the control $35a_4$ is in the "off" position, the switch 75 is inactive and does not communicate the condition of the air treatment preparation as programmed, e.g., present or absent, time to replace, etc.

Control $35a_5$ adjusts the timing of automatic activation of the apparatus 100. In some embodiments, it may be desirable to have the apparatus 100 dispense an air treatment preparation even if the apparatus 100 is not being activated to dry a user's hands, much like a traditional timed air freshening apparatus. In the present embodiment, the control $35a_5$ permits a user to configure the apparatus 100 to automatically activate to dispense air treatment preparation if the apparatus 100 has not been activated in 15 minutes, 1 hour (as presently shown), or 4 hours. That is, in the particular embodiment shown, if the apparatus 100 is not activated to dry a user's hands within 15 minutes, 1 hour, or 4 hours (depending on the selected setting) from the last activation, the apparatus 100 will, essentially, function as an air treatment preparation dispersion apparatus because the drying module will be automatically activated solely for the purpose of dispensing the air treatment preparation. In further embodiments, control $35a_5$ may have additional operable positions to allow further control over the automatic activation of the apparatus 100 for purposes of dispensing air treatment preparation.

The automatic activation of the apparatus 100 solely for the purpose of dispensing air treatment preparation is herein referred to as the "air treatment preparation only function," "air treatment preparation only activation," and similar terms. That is, the specific instance of activation is in response to inactivity of the apparatus 100 for a duration and the activation is not intended for drying a user's hands.

While control $35a_5$ presently has settings of 15 minutes, 1 hour and 4 hours, it will be readily appreciated that different settings and/or more or fewer settings may be provided. That is, the apparatus 100 is not limited by the particular time settings for the fragrance only function. Indeed, in some embodiments, the apparatus 100 may not have a control for the air treatment preparation only function, but rather be pre-programmed for the air treatment preparation only function. For example, in an embodiment a user will not be able to select a time setting for fragrance only activation; rather, the apparatus 100 will be pre-programmed to automatically activate after a given duration following a previous activation.

In an embodiment, the apparatus 100 is pre-programmed such that fan speed and the time of air treatment preparation only activation is optimized. That is, the fan speed and duration of air treatment preparation only activation is not customizable but rather calculated to achieve a balance of air treatment preparation dispersion and minimal energy usage. However, in further embodiments, an additional control may be provided to allow one to adjust the fan speed and/or time of activation for the air treatment preparation only function. Adjusting the fan speed and/or time of activation for the air treatment preparation only function will allow a user to customize the air treatment preparation only function to account for room size, room traffic, desired amount of odor control, and other preferences.

As mentioned, indicators 35b communicate various states/statuses of the apparatus 100. In the particular embodiment shown in FIG. 6, indicator $35b_1$ communicates whether the apparatus 100 is receiving power, e.g., lights up or turns off if apparatus 100 is receiving power depending on how the control module 30 is programmed. Indicator $35b_2$ communicates the status of the drying module 40, e.g., lights up or turns off when the drying module 40 is activated. Indicator $35b_3$ communicates the status of the air treatment preparation, e.g., as discussed above. That is, in some embodiments, the indicator $35b_3$ communicates whether an air treatment preparation is present or absent in the air treatment preparation module, e.g., lights up or turns off if the air treatment preparation is present or absent, depending on how the control module 30, and, indeed, switch 75 is programmed, and/or whether an air treatment preparation needs replacing, e.g., lights up or turns off if the air treatment preparation needs to be replaced. Similarly, indicator $35b_4$ communicates the status of the filter, e.g., as discussed above. That is, in some embodiments, the indicator $35b_4$ communicates whether a filter is present or absent in the filter module, e.g., lights up or turns off if the filter is present or absent, depending on how the control module 30, and, indeed, switch 65, is programmed, and/or whether a filter needs replacing, e.g., lights up or turns off if the filter needs to be replaced.

In a particular embodiment, indicators 35b are specifically designed to alert one that an action is needed or the apparatus is not working. In other words, in such embodiment, indicators 35b will not be lit when the apparatus is operational and no refill is needed.

Figure 1C:
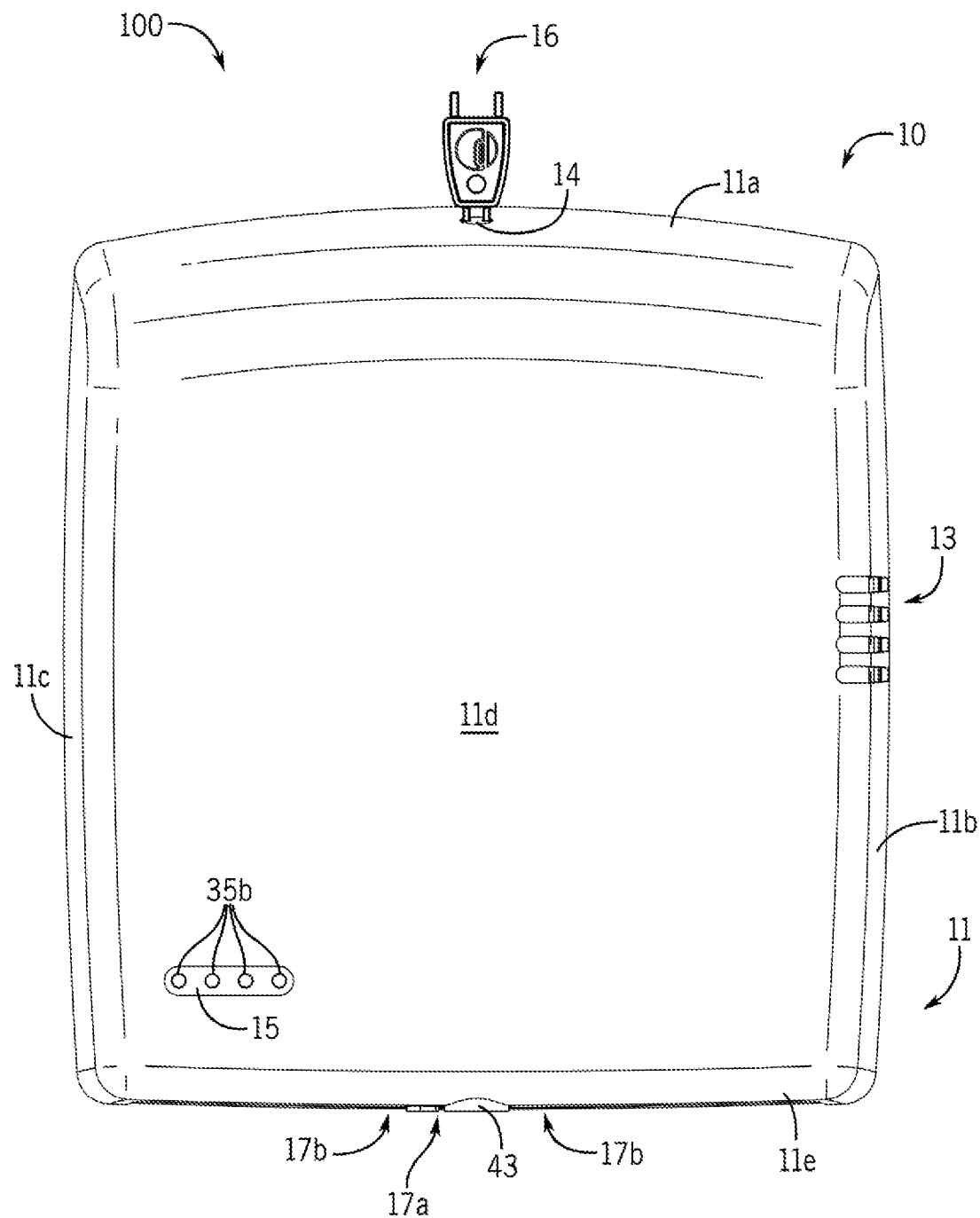
FIG. 1C is a further front view of the embodiment shown in FIG. 1B with the indicator lights visible, in accordance with embodiments of the present disclosure.
Figure 1D:
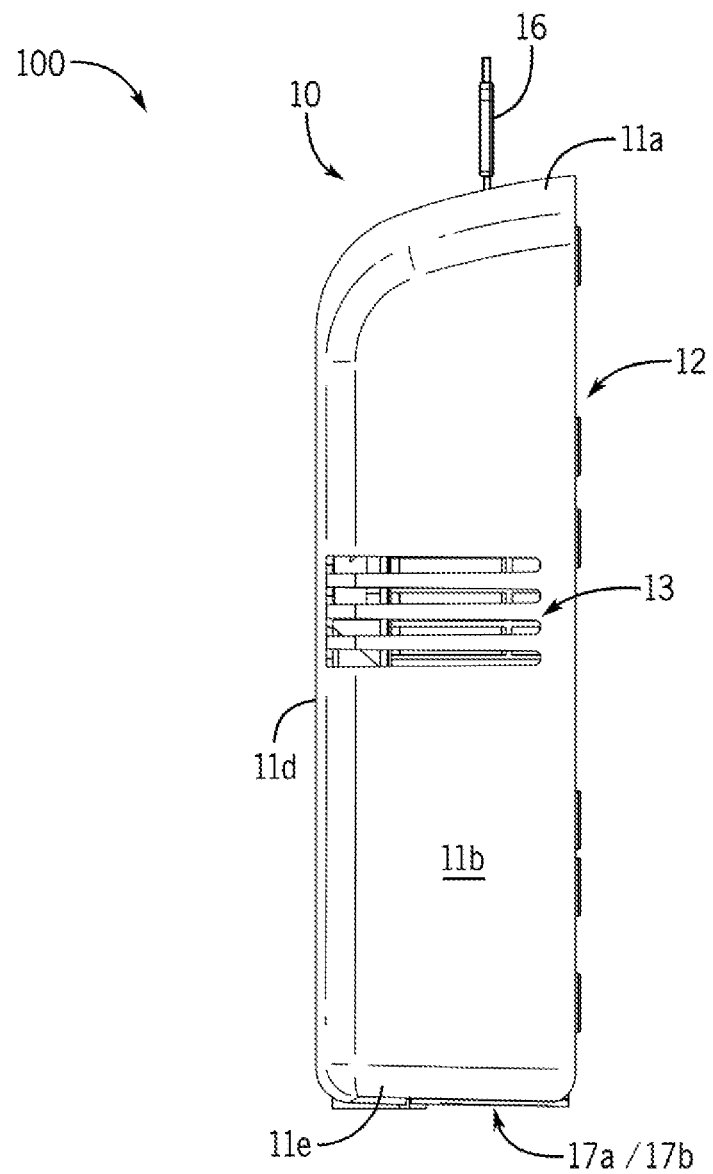
FIG. 1D is a right side view of the embodiment shown in FIG. 1A, in accordance with embodiments of the present disclosure.
Figure 1E:
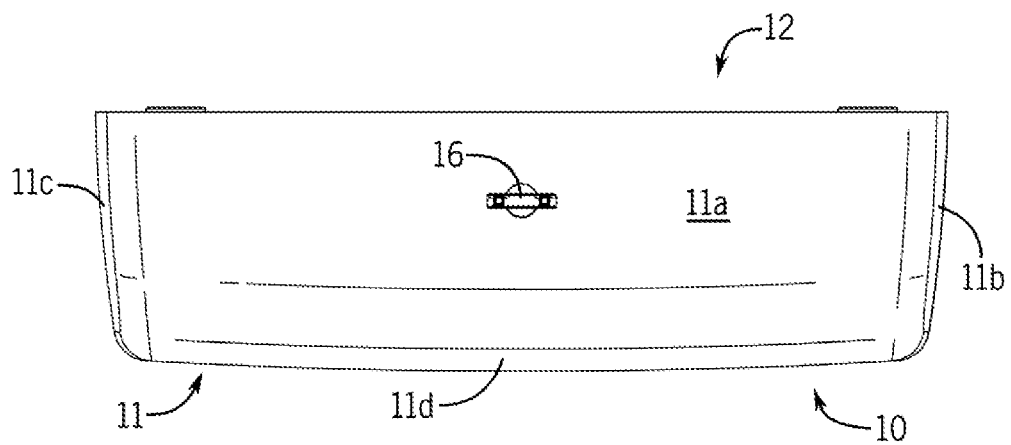
FIG. 1E is a top view of the embodiment shown in FIG. 1A, in accordance with embodiments of the present disclosure.
Figure 1F:
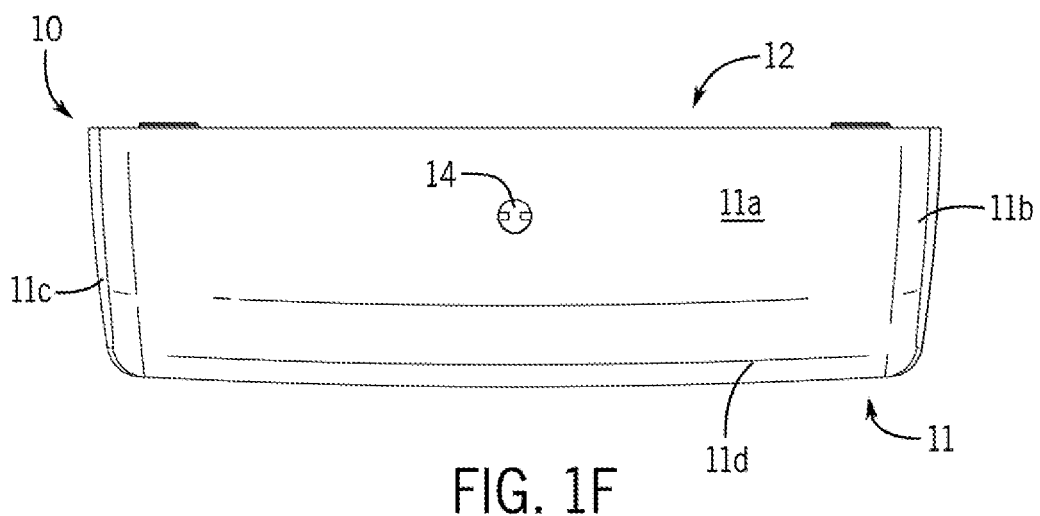
FIG. 1F is a top view of the embodiment shown in FIG. 1A with the key removed, in accordance with embodiments of the present disclosure.
Figure 2A:
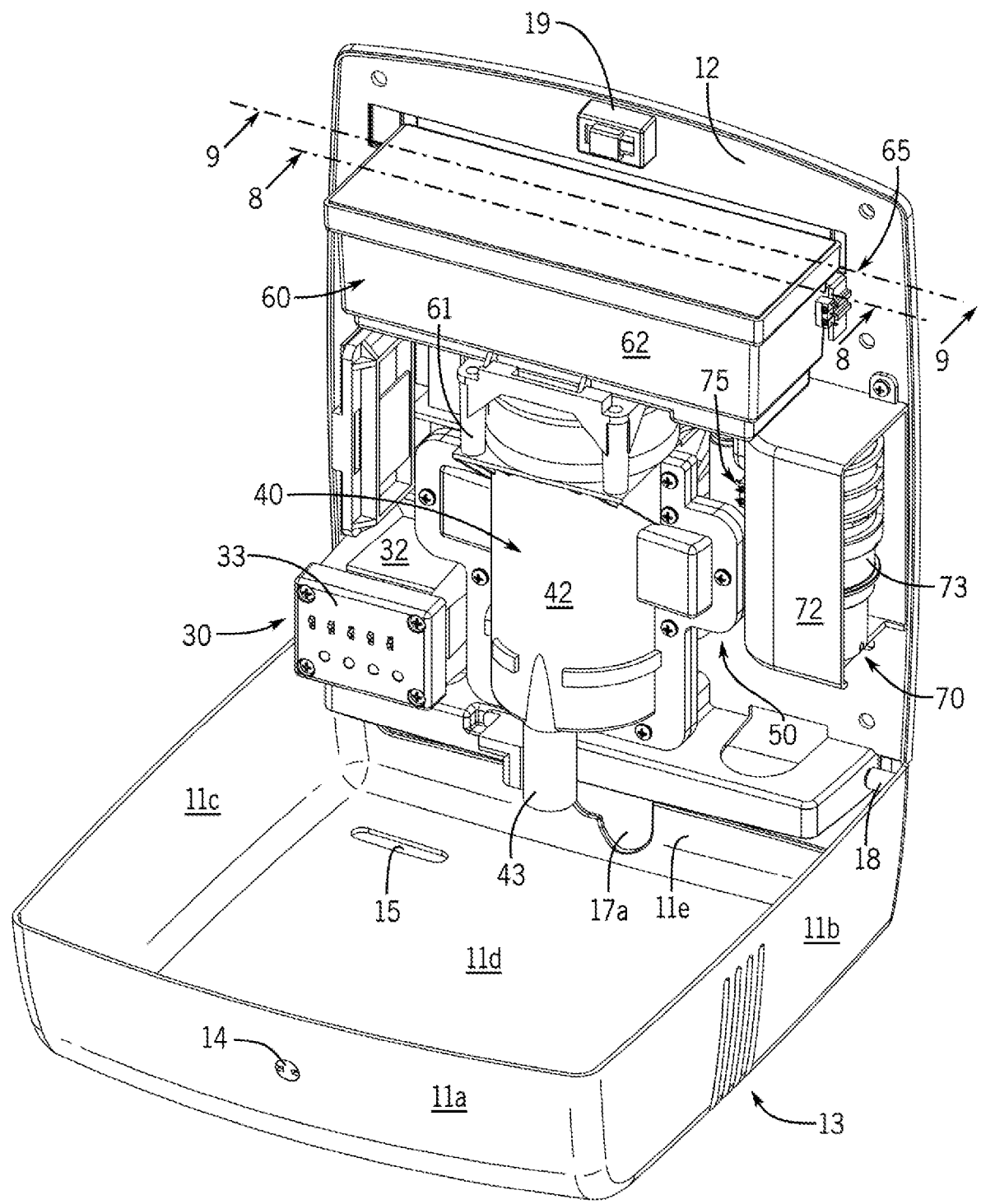
FIG. 2A is a perspective view of the embodiment shown in FIG. 1A with the front housing shown in the open position, in accordance with embodiments of the present disclosure.
Figure 2B:
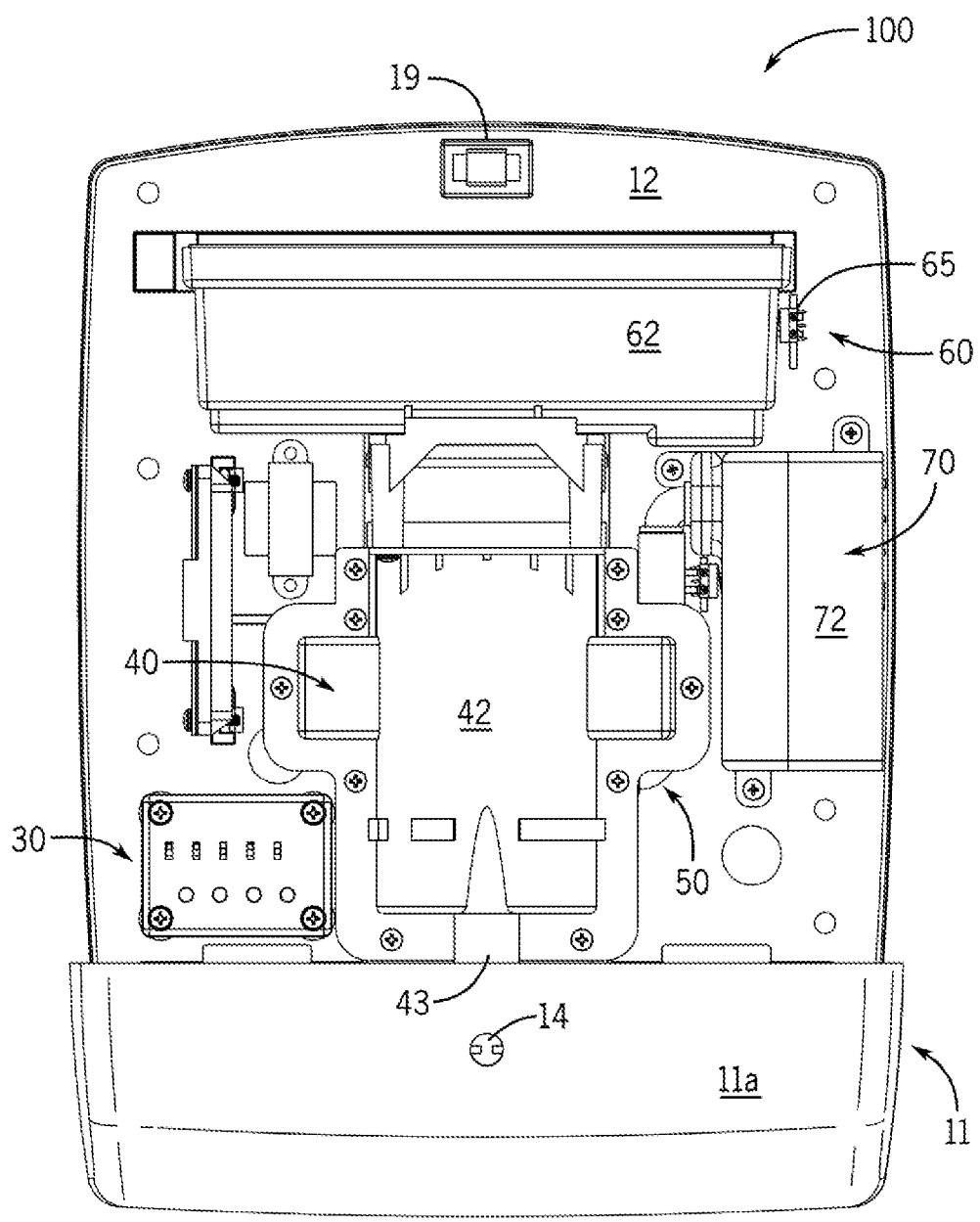
FIG. 2B is a front view of the embodiment shown in FIG. 2A, in accordance with embodiments of the present disclosure.
Figure 2C:
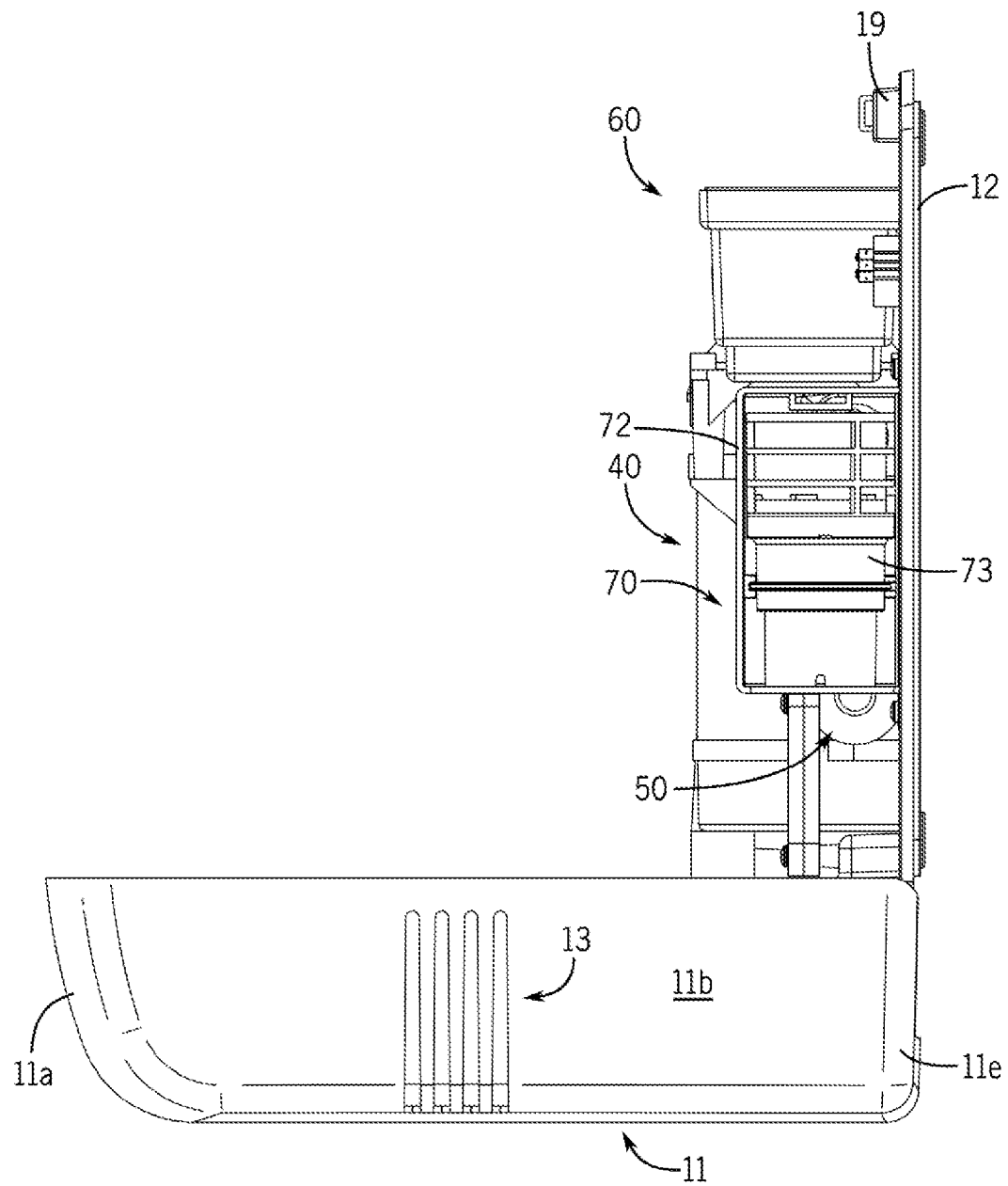
FIG. 2C is a right side view of the embodiment shown in FIG. 2A, in accordance with embodiments of the present disclosure.

As shown in FIG. 1C, in some embodiments one or more indicators 35b are visible through the housing 11 on the front panel 11d at the viewing port 15.

In the embodiment shown and described, the control panel 34 is described as having a plurality of switches and LED indicators. However, it is contemplated that the switches and indicators of the control panel may be replaced or supplemented with various applicable technologies including, for example, an LCD display in combination with buttons and/or switches, a touchscreen display, or combinations thereof. In further embodiments, the control panel 34 may communicate with various wireless or wired technologies (e.g., internet, Bluetooth™, etc.) to communicate statuses and/or accept remote instructions. For example, it is contemplated that a user may access the control panel via a mobile device to both check the apparatus's status and change one or more settings remotely, that is, the control panel will be configured to accept pushed data.

Turning again to FIGS. 2A-4 the drying module 40 includes a drying module housing 42. In the embodiment shown, the drying module housing 42 is provided as two pieces—a front drying module housing 42a which includes the air dispensing outlet 43, and the rear drying module housing 42b which includes the air diverter outlet 44. In particular, the air dispensing outlet 43 is positioned at the bottom of the front drying module housing 42a and the air diverter outlet 44 is positioned on a side of the rear drying module housing 42b. In further embodiments, however, both the air dispensing outlet 43 and air diverter outlet 44 may be disposed on the same portion of the drying module housing 42 and/or on the same side of any portion (or the same portion) of the drying module housing 42. Preferably, however, the air dispensing outlet 43 and air diverter outlet 44 are on different sides of the drying module housing 42.

In the embodiment shown, the air dispensing outlet 43 is shown as a cylindrical extension of the housing and the air diverter outlet 44 is shown as a male quick connect feature to allow the air diverter 50 to quickly and easily connect to the dryer housing 42. However, it will be appreciated that the air dispensing outlet 43 and air diverter outlet 44 can take any form suitable for permitting the passage of air from inside the drying module housing 42.

The drying module 40 further includes a motor unit 45 which includes the motor, fans, and other hardware necessary to render it operable to force airflow through outlets 43 and 44. In some embodiments, the motor unit 45 includes one or more heating elements (not shown). A screen 46 is disposed between the air dispensing outlet 43 and the outlet 45a of the motor unit 45 to prevent debris from entering the motor unit 45 via the air dispensing outlet 43. The inlet 45b of the motor unit 45 is in operable communication with the filter module 60 which filters air before it enters the motor unit 45. One or more gaskets 47 may be positioned between the motor unit 45 and/or the drying module housing 42 and the filter module 60. Further, in the embodiment shown, the drying module 40 and filter module 60 are connected by way of bracket 61 which secures to the drying module housing 42 (see, for example, FIG. 2A).

As described earlier, the air treatment preparation module 70 includes an air treatment preparation module housing 72 into which an air treatment preparation 73 is secured. The housing 72 has an air diverter inlet 76 (not shown) on one side and is open along another side, with the right side panel 11b of the housing 11 closing of the open side of the air treatment preparation module housing 72, as shown in FIGS. 1A-2B. In this way, the air treatment preparation module 70 is open the vents 13 to allow air treatment preparation to be dispensed into the air through the vents 13. The air treatment preparation module housing 72 connects to the housing back panel 12 using at least one securing device, such as a screw as shown in FIGS. 2A and 4.

The air diverter 50 connects the drying module 40 to the air treatment preparation module 70. In particular, the air diverter 50 connects the air diverter outlet 44 of the drying module 40 to the air diverter inlet 76 (not shown) of the air treatment preparation module 70. In the embodiment shown in FIG. 4, the air diverter 50 includes two angled segments 51a, 51b which are connected by a one-way valve 52 (which in the embodiment shown is a ball valve comprising ball 53), and a plurality of connection components (which in the embodiment shown include nuts 54a and washers 54b). Connection components 54a, 54b connect the angled segments 51a, 51b to the air diverter outlet 44 and air diverter inlet 76. The one way valve 52 connects to the angled segments 51a, 51b via interlocking structures. That is, structures on the exterior of the angled segments 51a, 51b interlock with structures on the interior of the one way valve 52 to secure the components together. However, it will be appreciated that other connections components and/or structures may be used to secure the components of the air diverter 50 to each other and the air diverter outlet 44 and air diverter inlet 76 (not shown) as necessary.

Figure 7:
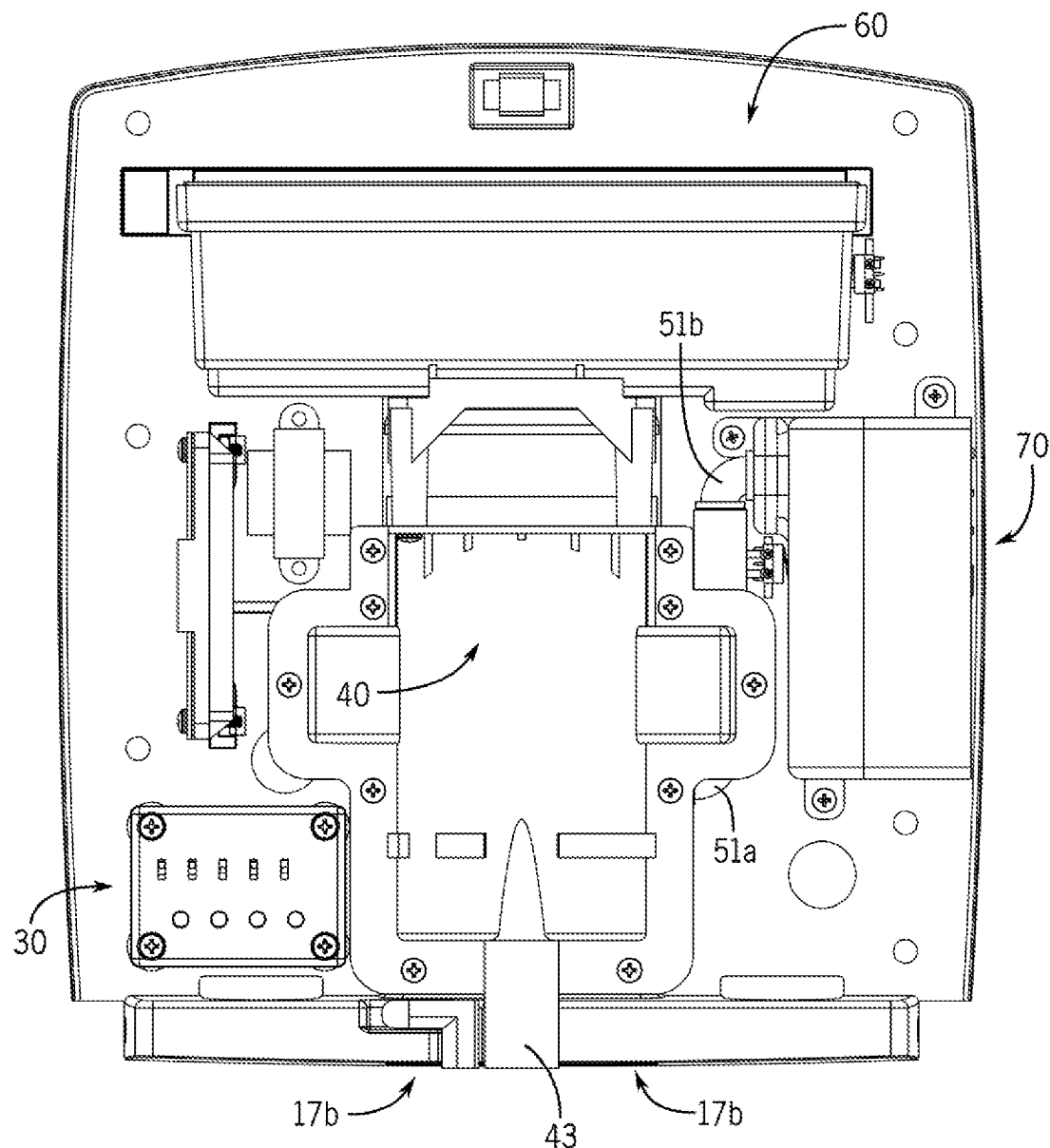
FIG. 7 is a front view of the apparatus with the front of the housing removed for clarity, in accordance with embodiments of the present disclosure.

FIG. 7 shows the interior of the apparatus 100 with the housing cover 11 removed for clarity. Control module 30 is shown with the control module covering 33 and control panel 34 secured to the control module housing 32, which is integral with the housing back panel 12. The filter module 60, drying module 40 and air treatment preparation module 70 are also each secured to the housing back panel 12. The filter module 60 is in position at the inlet 54b of the motor unit 45 (not shown) such that air pulled into the motor unit 45 upon activation of the drying module 40 passes through the filter. The air dispensing outlet 43 is positioned at the opening 17a of the bottom panel 11e (not shown) of the housing cover 11 to allow air to be dispensed out of the apparatus 100, e.g., to dry a user's hands positioned under the opening 17a. Hose segment 51a is shown connecting the air diverter outlet 44 (not shown) of the drying module 40 to the air diverter inlet 76 (not shown) of the air treatment preparation module 70.

Figure 8A:
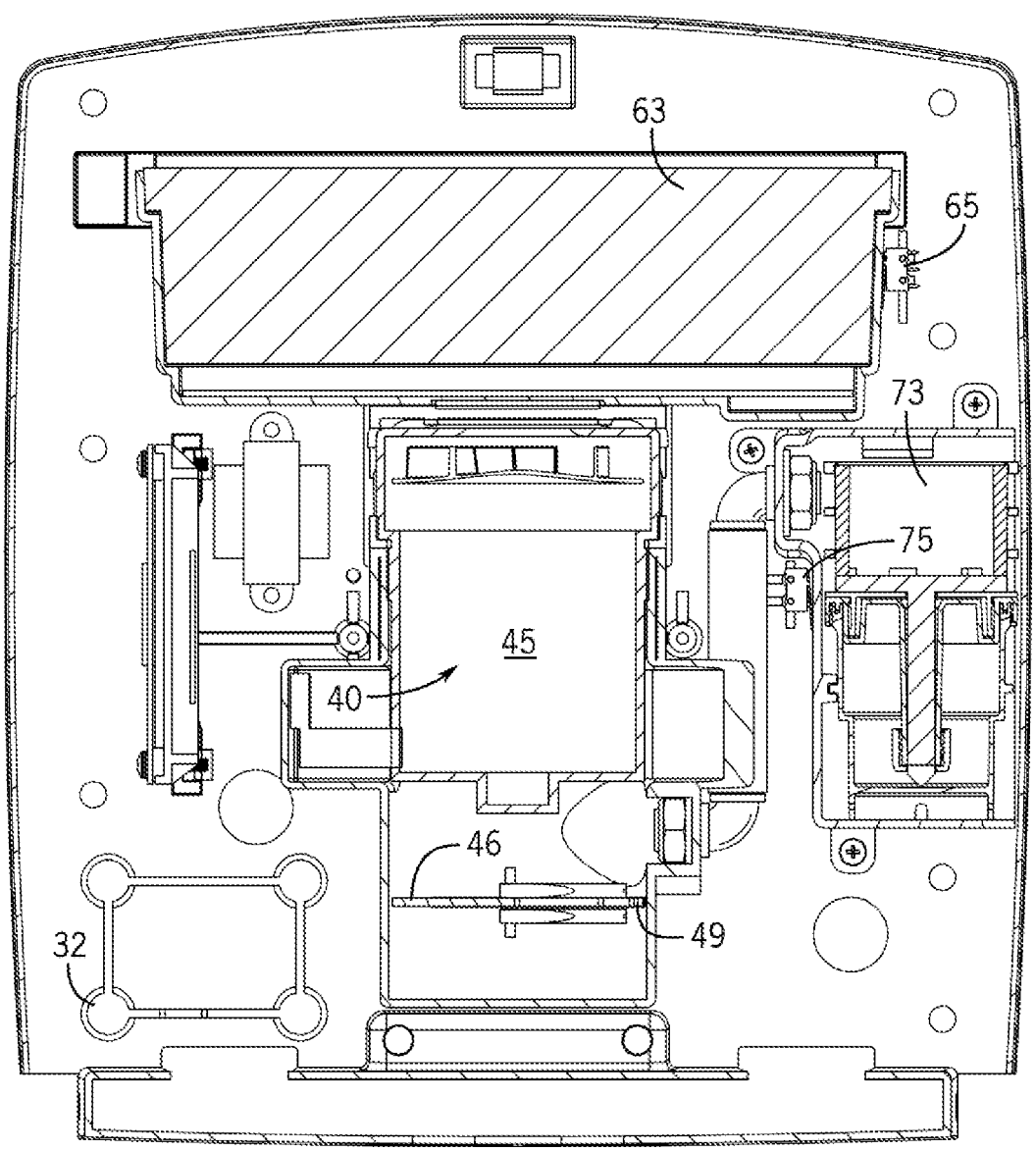
FIG. 8A is a cross-sectional view of the apparatus shown in FIG. 2A taken along line 8-8, in accordance with embodiments of the present disclosure.

FIG. 8A is a cross-sectional view of the apparatus 100, which particularly shows the filter module switch 65 engaged with a filter 63 and the air treatment preparation module switch 65 engaged with an air treatment preparation 73. As shown in FIG. 8A, the switches 65 and 75 are both mechanical switches, and, in particular, miniature snap-action switches, such as those available under the tradename Micro Switch, available from Honeywell. However, in further embodiments, other types of mechanical switches may be used and, in some embodiments, potentially one or more electronic switches.

Further shown is the positioning of the screen 46 within the drying module housing 42. In particular, the screen 46 is secured in position by engagement with groove 49, which extends at least partially around the interior of the front drying module housing 42a and the rear drying module housing 42b, such as also shown in FIG. 4.

Figure 8B:
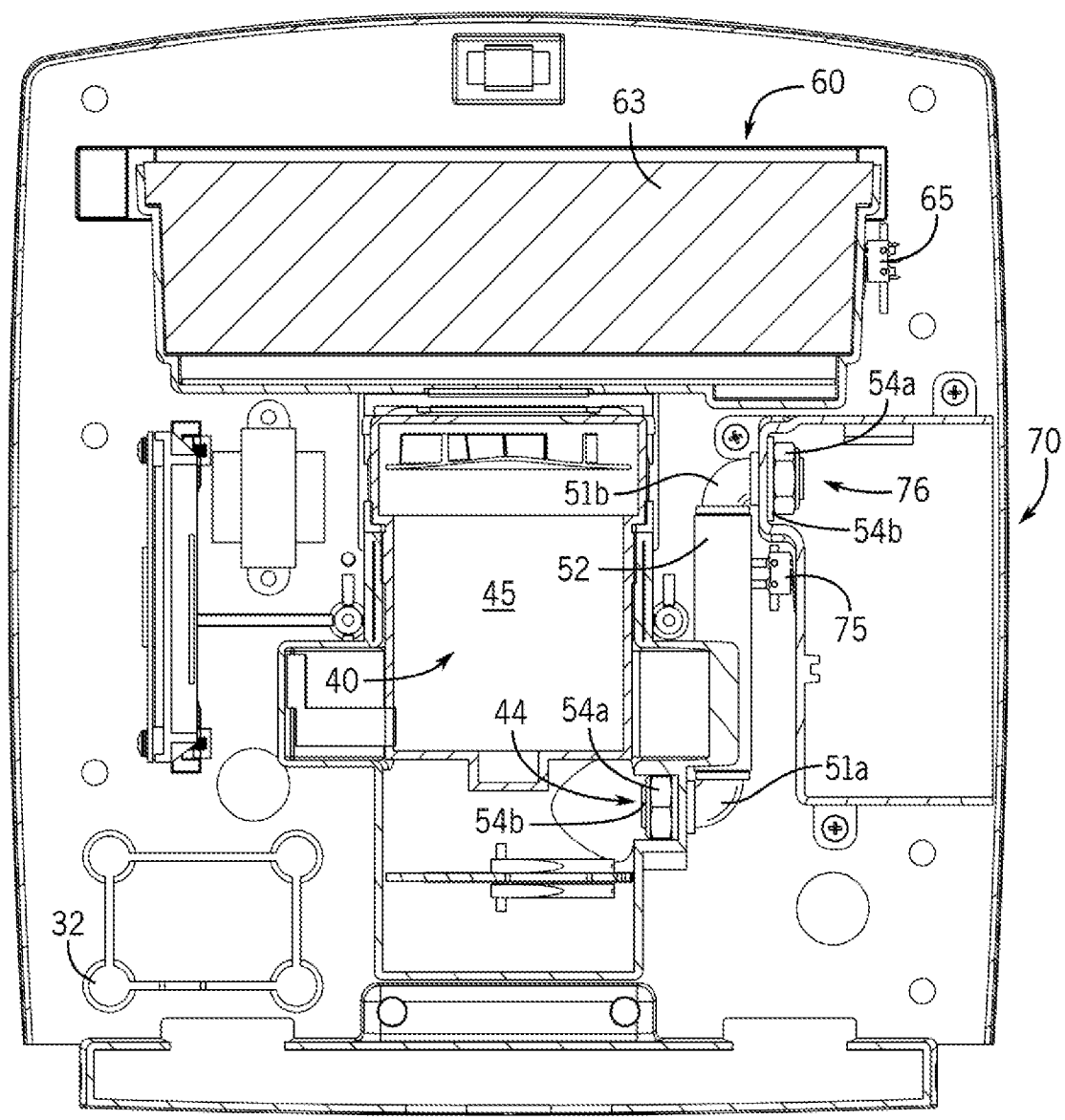
FIG. 8B is the cross-sectional view shown in FIG. 8A with the air treatment preparation module removed, in accordance with embodiments of the present disclosure.

FIG. 8B is the same cross-sectional view of the apparatus 100 as shown in FIG. 8A; however, in FIG. 8B, the air treatment preparation 73 has been removed. With no air treatment preparation 73 in the air treatment preparation module 70, the air treatment preparation module switch 75 is not activated.

Figure 9A:
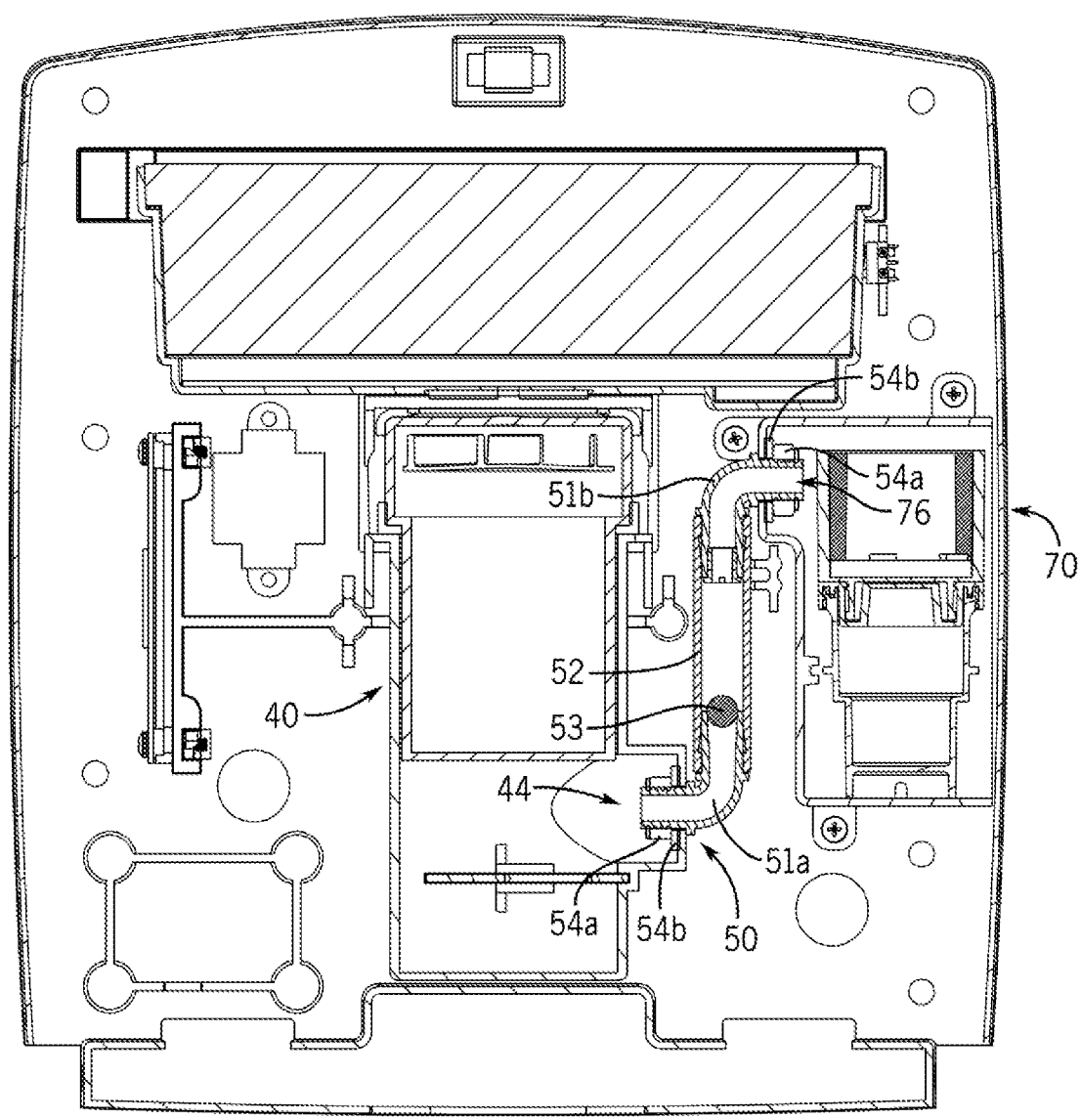
FIG. 9A is a further cross-sectional view of the apparatus shown in FIG. 2A taken along the line 9-9 showing the valve assembly in the closed position, in accordance with embodiments of the present disclosure.
Figure 9B:
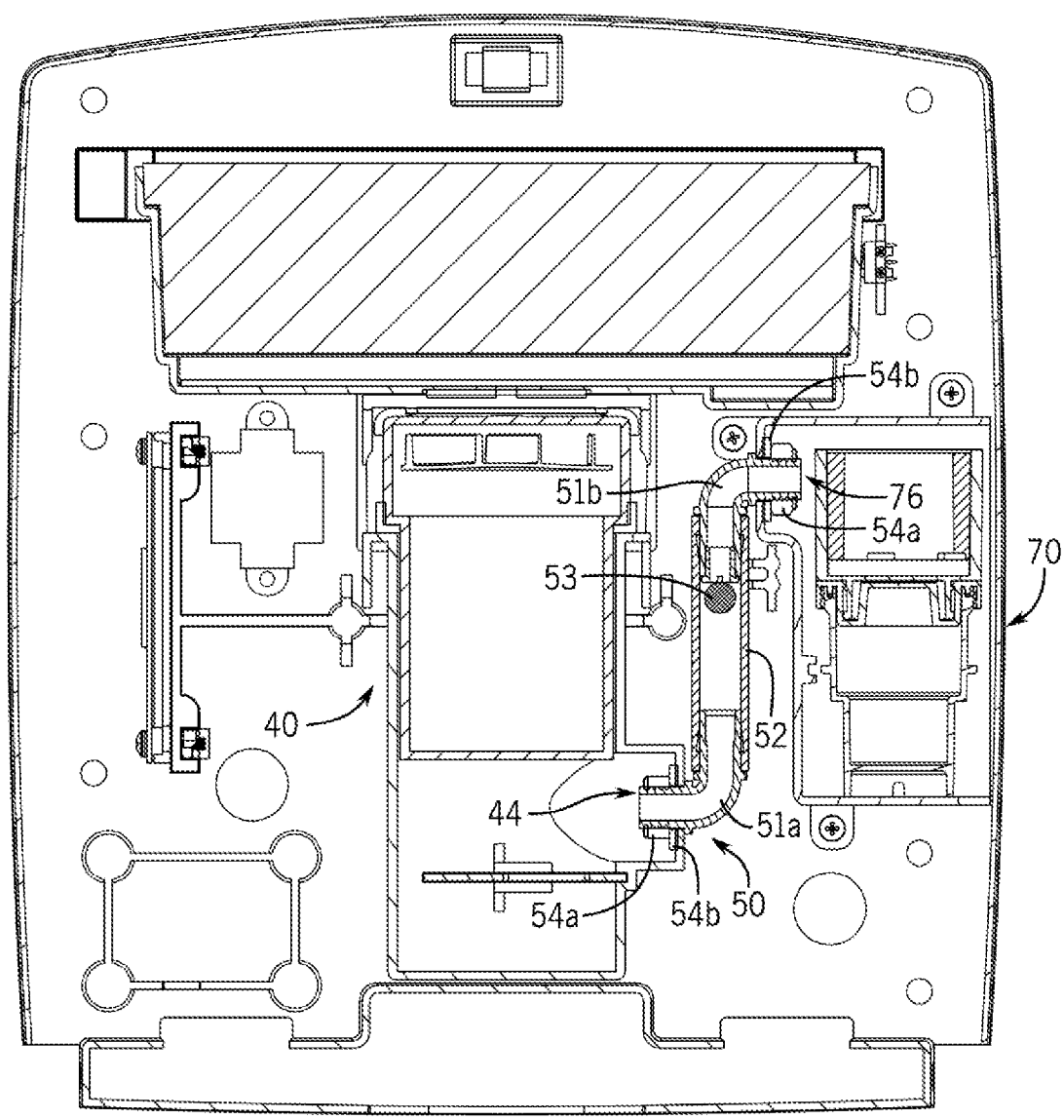
FIG. 9B is the cross-sectional view of FIG. 9A showing the valve assembly in the open position, in accordance with embodiments of the present disclosure.
Figure 10A:
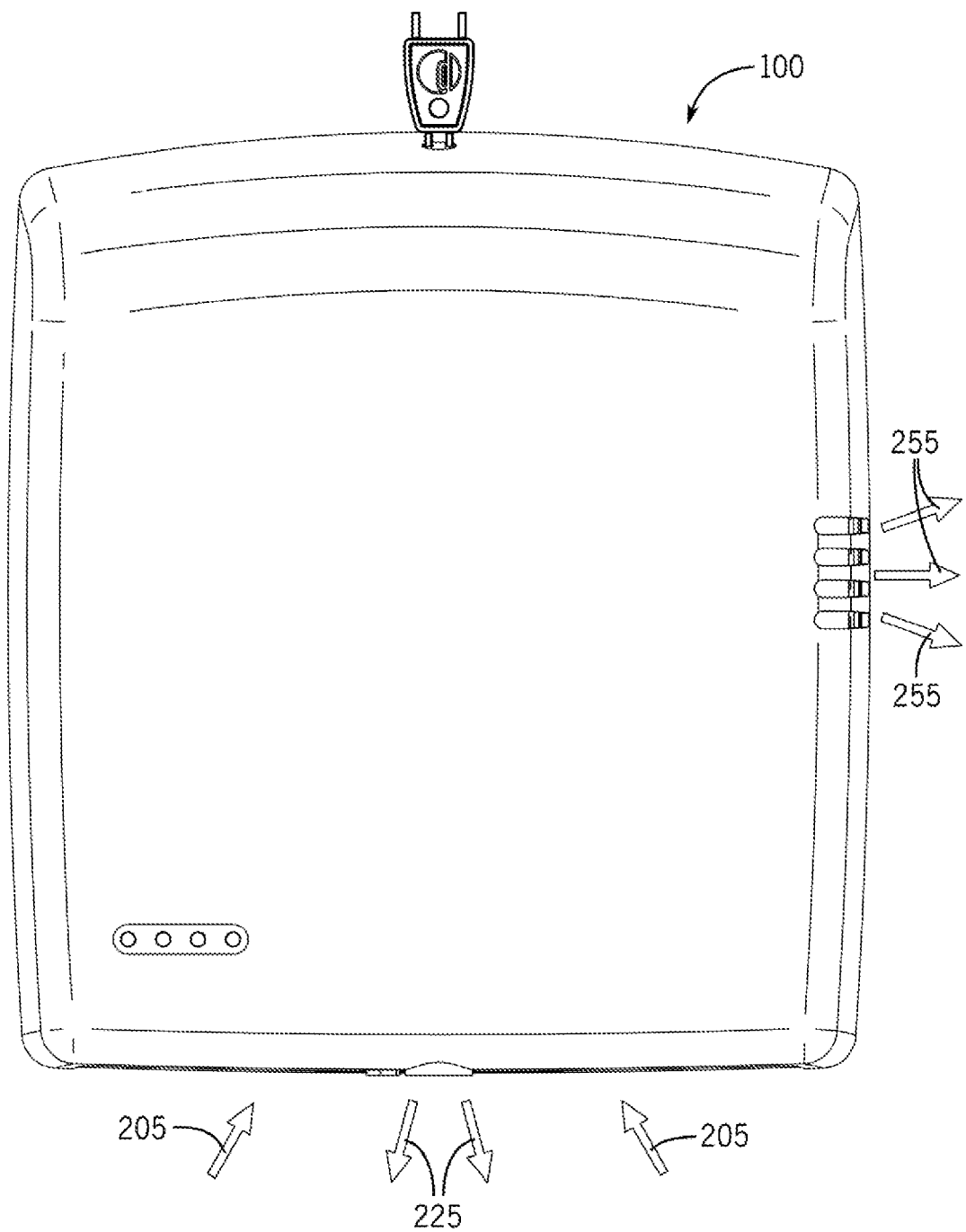
FIG. 10A is an external view of an apparatus for dispensing air and an air treatment preparation illustrating airflow through the apparatus, in accordance with embodiments of the present disclosure.
Figure 10B:
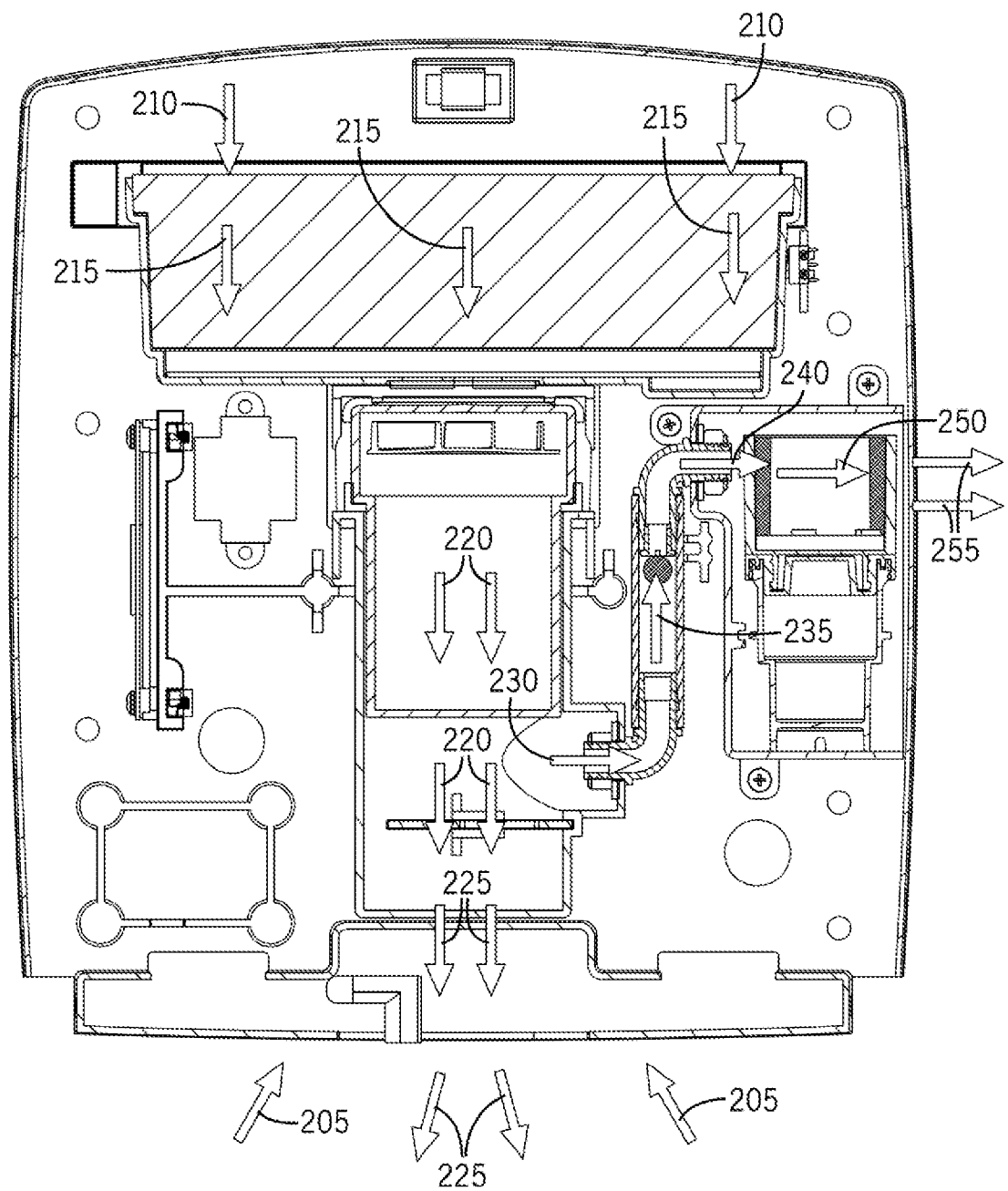
FIG. 10B is an internal schematic drawing illustrating airflow through an apparatus for dispensing air and an air treatment preparation, in accordance with embodiments of the present disclosure.

FIGS. 9A and 9B are further cross-sectional view of the apparatus 100 and show the structure of the air diverter outlet 44 of the drying module 40 and the air diverter inlet 76 of the air treatment preparation module 70. As shown, both the air diverter outlet 44 and air diverter inlet 76 are openings in the respective structures through which the angled segments 51a, 51b are inserted. The air diverter outlet end of the angled segment 51a and the air diverter inlet end of the angled segment 51b contain threads followed by a flange having a height sufficient make the diameter of the respective angled segment at the point of the baffle greater than the diameter of the corresponding air diverter outlet 44 or air diverter inlet 76. As a result, the angled segments 51a, 51b are prevented from projecting too far into the air diverter outlet 44 and air diverter inlet 76, respectively, and are secured in position by tightening baffle against the outside of the corresponding structure (e.g., drying module housing or air treatment preparation module housing) using the connection components 54a, 54b.

It will be appreciated that, in further embodiments, the air diverter outlet 44 and air diverter inlet 76 may take different forms (e.g., male or female quick-connect style connections, etc.) and the angled segments 51a, 51b may likewise take alternative forms in order to enable the connection of the angled segments 51a, 51b to the corresponding air diverter outlet 44 and air diverter inlet 76.

With further reference to FIGS. 9A and 9B, and as described previously, the air diverter 50 comprises a first angled segment 51a, a second angled segment 51b, and a one-way valve 52 comprising a ball 53. A first end of the angled segment 51a is connected to the air diverter outlet 44 of the drying module 40 and a second end of the angled segment 51a is connected to the one-way valve 52. Similarly, the angled segment 51b is connected to both the one-way valve 52 and the air diverter inlet 76. Specifically, a first end of the angled segment 51b is connected to the one-way valve 52 and a second end of the hose segment 51*b* is connected to the air diverter inlet 76 of the air treatment preparation module 70.

In the embodiment shown, the one-way valve 52 is a ball valve comprising a ball 53. However, any style of one-way valve could be used provided air flow from the drying module 40 to the air treatment preparation module 70 is permitted and air flow from the air treatment preparation module 70 to the drying module 40 is prohibited.

In the view shown in FIG. 9A, the one-way valve 52 is closed. That is, there is not enough force caused by air flow from the drying module 40 to the air treatment preparation module 70 to push the ball 53 of the ball valve 52 upwards and open the valve 52. In such instances, the drying module 40 may be off (e.g., not activated), or the drying module may be running at such a low speed that there is not enough air pressure generated to open the one-way valve 52 (e.g., the drying module 40 may be configured for low speed (i.e., longer drying time), or just activated or just turning off). However, in the view shown in FIG. 9B, the valve 52 is open, i.e., the ball 53 is in the up position. Once a threshold force (i.e., air pressure) is present, the ball 53 is forced up, thereby opening the valve 52 and permitting air flow through the air diverter 50 and from the drying module 40 through the air treatment preparation module 70. Reverse flow of air is prohibited, however, by the use of the one-way valve 52. In the particular example shown, in which the one-way valve is a ball valve, once the air pressure pushing up on the ball 53 drops below a threshold value, or there is air flow from the air treatment preparation module 70 pushing down on the ball 53, the ball drops and closes the valve. In other words, the apparatus 100 utilizes the energy of the drying module to also actively dispense an air treatment preparation. This saves energy, and therefore money, compared to devices which utilize a separate motor or similar mechanism to actively dispense air treatment preparation.

FIGS. 10A and 10B illustrate airflow through an apparatus 100 and a method of treating air using an apparatus for dispensing air and an air treatment preparation 100, in accordance with embodiments of the present disclosure.

First, the apparatus for dispensing air and an air treatment preparation 100 is activated. Activation may be initiated by a user, such as by pressing a button or by activation of a motion sensor or light sensor (e.g., as with automatic hand driers). In other embodiments, activation may be initiated by the apparatus 100 itself, such as, for example, when the apparatus 100 is configured to automatically dispense an air treatment preparation if the apparatus 100 is not used or activated for a given amount of time.

Once the apparatus 100 is activated, the drying module 40 activates and the motor begins to pull air through its inlet from the environment 205.

In the embodiment shown, the air inlets are on the bottom of the apparatus 100 and air is pulled in and drawn up through the back of the housing. However, in further embodiments, one or more air inlets may be provided at other locations of the housing and have one or more defined paths through the housing to reach the filter and/or drying module, provided cross-contamination with air having been treated with the air treatment preparation is avoided (e.g., air inlet is not on same side of the housing as the vents or other structure(s) through which air treatment preparation is dispersed. In the embodiment shown, the air first passes through the filter module. That is, the air drawn in through the bottom of the apparatus is pulled to the top of the apparatus to enter the filter from above 210 and is drawn down through the filter 215. However, it will be appreciated that, in further embodiments, the filter module may be omitted, or a filter not installed in the filter module.

The motor forces the (filtered) air through the drying module 220 and a maj ority of the air exits the drying module at the air dispensing outlet 225, such as, for example, to dry a user's hands. However, a portion of the air flow is diverted through the air diverter outlet 230.

Air from the air diverter outlet is directed toward the one-way valve in the air diverter. Once the air pressure in the air diverter on the drying module-side of the air diverter reaches a certain threshold pressure, the one-way valve is tripped 235 and the valve opens to permit airflow into the air treatment preparation module 240. The air enters the air treatment preparation module and passes over (so as to contact and carry a portion of the air treatment preparation) the air treatment preparation 250 and exits the apparatus 100 through the vents in the side panel of the housing cover 255. When passing through the air treatment preparation module, the air comes in contact with the air treatment preparation, when present, and carries a quantity of the air treatment preparation with it as the air exits the apparatus 100.

Once the air pressure in the air diverter on the drying module-side of the air diverter drops below the threshold amount, the one-way valve closes to prohibit air flow from the air treatment preparation module back into the drying module. Similarly, if the air pressure in the air diverter on the air treatment preparation module-side of the air diverter is greater than the air pressure in the air diverter on the drying module-side of the air diverter, the one-way valve closes to prevent air flow from the air treatment preparation module to the drying module.

It is specifically intended that the present disclosure not be limited to the embodiments and illustrations contained herein, but include modified forms of those embodiments including portions of the embodiments and combinations of elements of different embodiments as come within the scope of the following claim.

What is claimed is:

1. An apparatus for dispensing air and an air treatment preparation comprising:

a housing having a housing back panel and a housing cover releasably attached to the housing back panel, wherein the housing cover includes a bottom panel having an opening and a side panel having a plurality of vents;

a drying module having an inlet, an air dispensing outlet, and an air diverting outlet, wherein the air dispensing outlet is aligned with the opening in the bottom panel of the housing cover;

an air treatment preparation module having an air diverting inlet and the air treatment preparation, wherein the air treatment preparation is exposed to the plurality of vents; and an air diverter connecting the air diverting outlet and air diverting inlet, the air diverter further including a one-way valve.

2. The apparatus of claim 1, further comprising a filter module connected to the inlet of the drying module.

3. The apparatus of claim 1, wherein the air treatment preparation is selected from the group consisting of an air fragrance, an air deodorizer, and combinations thereof.

4. The apparatus of claim 1, wherein the filter module further includes a mechanical switch.

5. The apparatus of claim 1, wherein the air treatment preparation module further includes a mechanical switch.

6. The apparatus of claim 1, further comprising a control module having at least one control and at least one indicator.

7. The apparatus of claim 6, wherein the at least one indicator has at least two operable positions.

8. The apparatus of claim 6, wherein the at least one of the filter module and air treatment module further includes a mechanical switch.

9. The apparatus of claim 8, wherein the at least one indicator is in operable communication with the mechanical switch of the at least one of the filter module and the air treatment preparation module.

10. A method of dispensing an air treatment preparation, the method comprising:

activating an apparatus comprising:

a housing having a housing back panel and a housing cover releasably attached to the housing back panel, wherein the housing cover includes a bottom panel having an opening and a side panel having a plurality of vents;

a drying module comprising a motor, an air dispensing outlet and an air diverter outlet, an air treatment preparation module comprising an air diverter inlet and the air treatment preparation, and an air diverter connecting the air diverter outlet of the drying module and the air diverting inlet of the air treatment preparation module, the air diverter further including a one-way valve;

forcing air, using the motor, through the drying module, wherein a majority portion of the air is forced through the air dispensing outlet and a minor portion of the air is forced through the air diverter inlet and out through the plurality of vents in the side panel;

building air pressure in the air diverter to reach a threshold level to open the one-way valve;

opening the one way valve, thereby permitting air flow through the air diverter and into the air treatment preparation module;

contacting the air treatment preparation with at least a portion of the minor portion of the air; and forcing the minor portion of the air out of the air treatment preparation module.

\* \* \* \* \*